US012605038B2

(12) United States Patent
Lin et al.

(10) Patent No.: US 12,605,038 B2
(45) Date of Patent: Apr. 21, 2026

(54) ENDOSCOPIC IMAGE PROCESSING METHOD

(71) Applicant: LUXVISIONS INNOVATION TECHNOLOGY CORP. LIMITED, Guangzhou City (CN)

(72) Inventors: Chih-Ju Lin, Guangzhou (CN); Hong-Hsien Chou, Guangzhou (CN)

(73) Assignee: GUANGZHOU LUXVISIONS INNOVATION TECHNOLOGY CORP. LIMITED, Guangzhou City (CN)

( * ) Notice: Subject to any disclaimer, the term of this patent is extended or adjusted under 35 U.S.C. 154(b) by 0 days.

(21) Appl. No.: 18/963,565

(22) Filed: Nov. 28, 2024

(65) Prior Publication Data

US 2025/0375093 A1     Dec. 11, 2025

Related U.S. Application Data

(60) Provisional application No. 63/658,451, filed on Jun. 11, 2024.

(30) Foreign Application Priority Data

Sep. 23, 2024    (CN) .......................... 202411326627.6

(51) Int. Cl.
    *A61B 1/06*          (2006.01)
    *A61B 1/00*          (2006.01)
    (Continued)
(52) U.S. Cl.
    CPC ........ *A61B 1/000095* (2022.02); *A61B 1/046* (2022.02); *G06T 5/90* (2024.01);
         (Continued)

(58) Field of Classification Search
    CPC ......... G06T 5/90; G06T 11/001; G06T 11/60; G06T 2207/10024; G06T 2207/10048;
         (Continued)

(56) References Cited

U.S. PATENT DOCUMENTS

| | | | |
|---|---|---|---|
| 9,888,835 B2 | 2/2018 | Rehe | |
| 2015/0208958 A1* | 7/2015 | Kaku | ................. A61B 5/14551 |
| | | | 382/128 |

(Continued)

FOREIGN PATENT DOCUMENTS

| | | |
|---|---|---|
| CN | 103927727 A | 7/2014 |
| CN | 221105783 | 6/2024 |
| TW | 202217280 A | 5/2022 |

OTHER PUBLICATIONS

"Office Action of Taiwan counterpart Application", issued on Oct. 28, 2025, p. 1-p. 9.

*Primary Examiner* — Baisakhi Roy
(74) *Attorney, Agent, or Firm* — JCIPRNET

(57) ABSTRACT

An endoscopic image processing method suitable for using an endoscope to capture images of diseased parts, which comprises following steps: providing a first image and a second image of the diseased parts, wherein wavelengths or polarized angles of the first image and the second image are different; performing binary image processing on the second image; performing multiply processing on the second image to produce a first multiply image according to a result of the binary image processing; performing pseudo-color processing on the first multiply image to produce a first pseudo-color processed image; and integrating the first pseudo-color processed image with the first image to produce a first integrated image. The endoscopic image processing method acquires images with a plurality of bands or polarized angles (Continued)

of a same area, and improves endoscopic image quality of the diseased parts by processing and integrating these images.

10 Claims, 5 Drawing Sheets

(51) Int. Cl.

| | | |
|---|---|---|
| *A61B 1/04* | (2006.01) | |
| *A61B 5/00* | (2006.01) | |
| *G06T 5/90* | (2024.01) | |
| *G06T 11/00* | (2006.01) | |
| *G06T 11/60* | (2006.01) | |

(52) U.S. Cl.
CPC ............ *G06T 11/001* (2013.01); *G06T 11/60* (2013.01); *G06T 2207/10024* (2013.01); *G06T 2207/10048* (2013.01); *G06T 2207/10068* (2013.01); *G06T 2207/20221* (2013.01)

(58) Field of Classification Search
CPC . G06T 2207/10068; G06T 2207/20221; A61B 1/000095; A61B 1/046
See application file for complete search history.

(56) References Cited

U.S. PATENT DOCUMENTS

| | | | | |
|---|---|---|---|---|
| 2015/0366444 | A1* | 12/2015 | Morimoto ............ | A61B 1/0655 |
| | | | | 600/339 |
| 2018/0042468 | A1* | 2/2018 | Teramura ............... | H04N 23/74 |
| 2021/0266508 | A1* | 8/2021 | Deguchi ............... | G06T 11/001 |
| 2022/0390383 | A1* | 12/2022 | Sakane .................. | G03B 33/08 |
| 2024/0081616 | A1* | 3/2024 | Saito ................... | A61B 1/0638 |
| 2024/0341641 | A1* | 10/2024 | Saito ................... | A61B 5/1459 |
| 2024/0371052 | A1* | 11/2024 | Kishine ................. | H04N 23/55 |

* cited by examiner

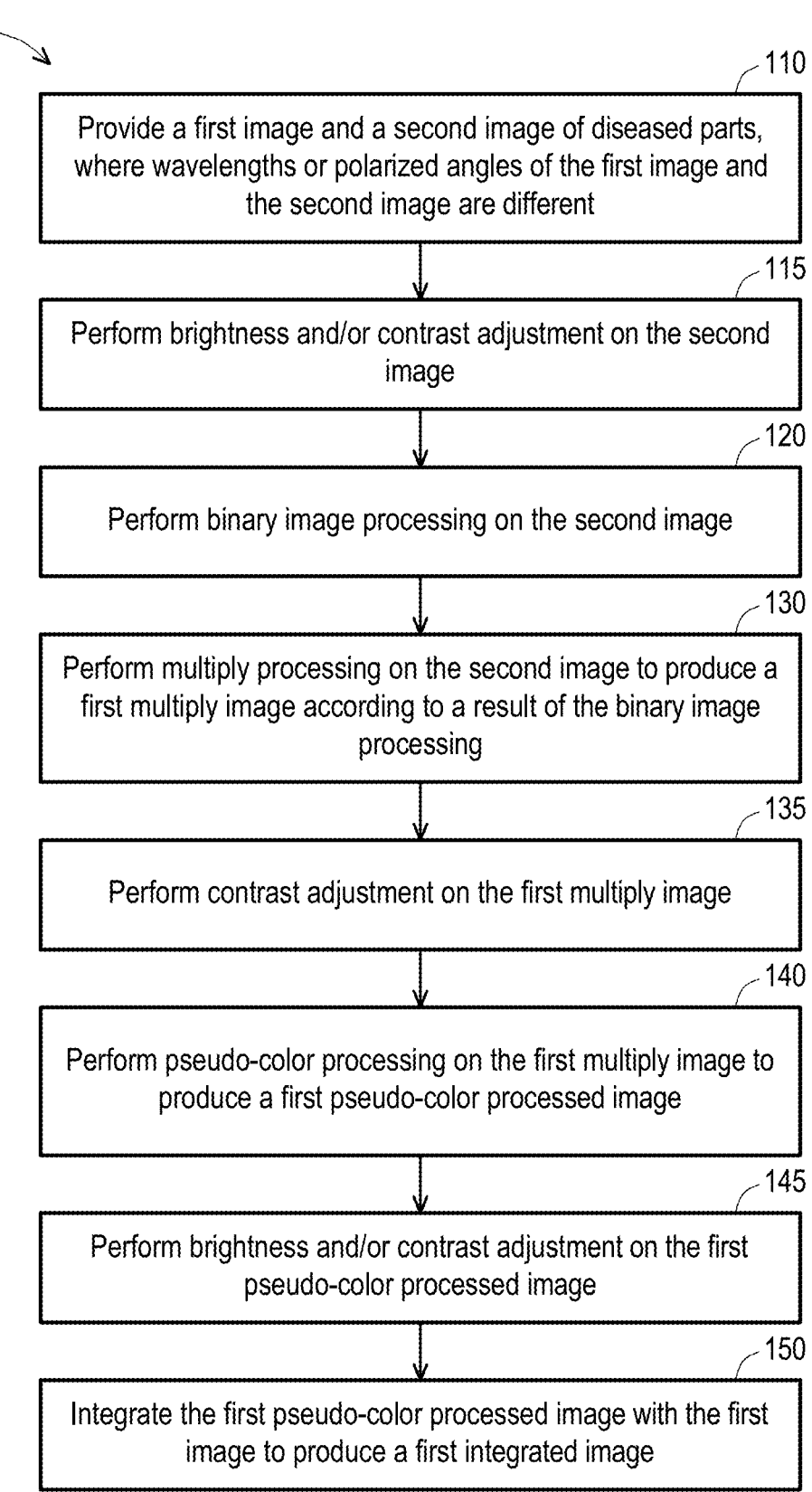

100

110
Provide a first image and a second image of diseased parts, where wavelengths or polarized angles of the first image and the second image are different 115
Perform brightness and/or contrast adjustment on the second image 120
Perform binary image processing on the second image 130
Perform multiply processing on the second image to produce a first multiply image according to a result of the binary image processing 135
Perform contrast adjustment on the first multiply image 140
Perform pseudo-color processing on the first multiply image to produce a first pseudo-color processed image 145
Perform brightness and/or contrast adjustment on the first pseudo-color processed image 150
Integrate the first pseudo-color processed image with the first image to produce a first integrated image

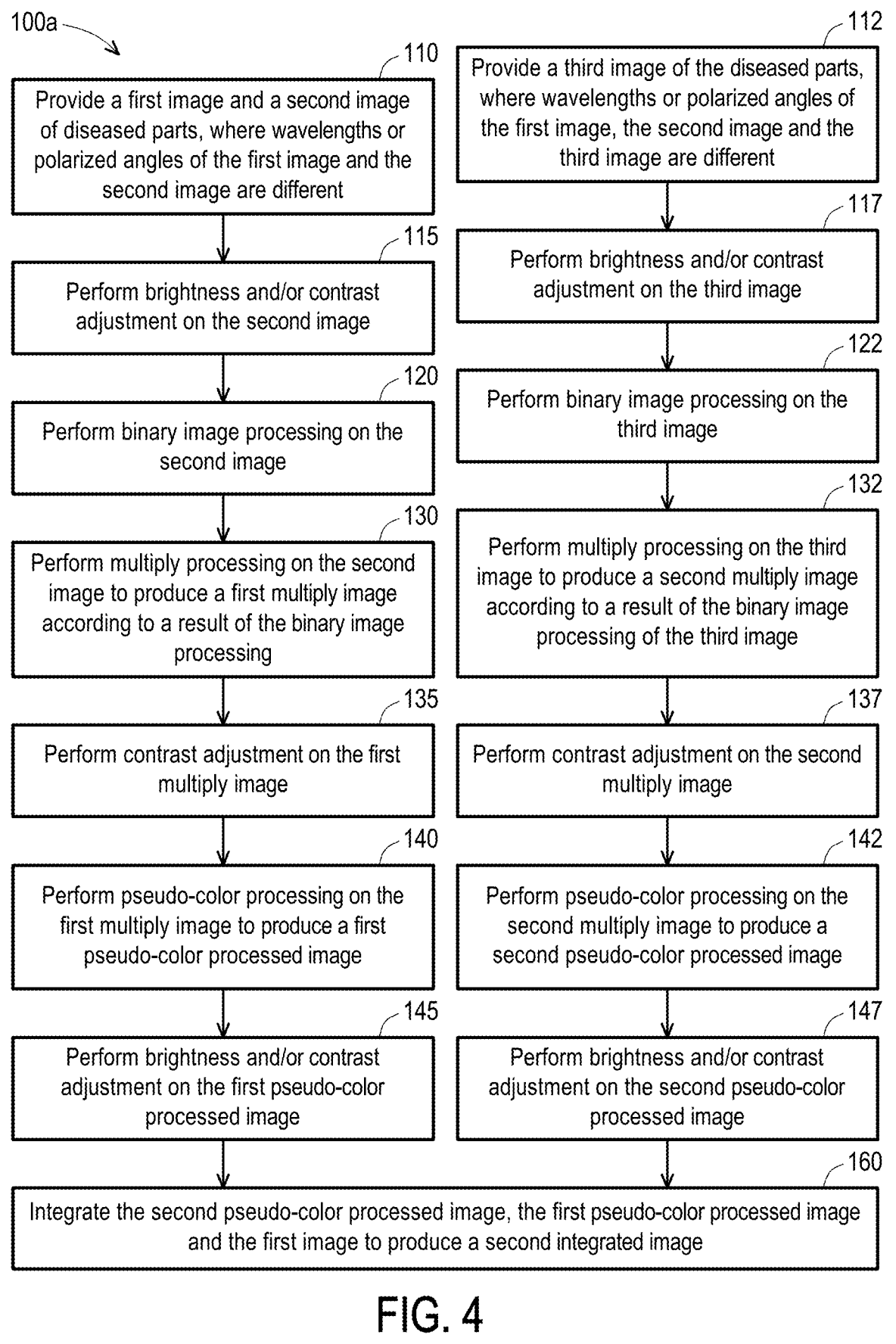

110
Provide a first image and a second image of diseased parts, where wavelengths or polarized angles of the first image and the second image are different 112
Provide a third image of the diseased parts, where wavelengths or polarized angles of the first image, the second image and the third image are different 115
Perform brightness and/or contrast adjustment on the second image 117
Perform brightness and/or contrast adjustment on the third image 120
Perform binary image processing on the second image 122
Perform binary image processing on the third image 130
Perform multiply processing on the second image to produce a first multiply image according to a result of the binary image processing 132
Perform multiply processing on the third image to produce a second multiply image according to a result of the binary image processing of the third image 135
Perform contrast adjustment on the first multiply image 137
Perform contrast adjustment on the second multiply image 140
Perform pseudo-color processing on the first multiply image to produce a first pseudo-color processed image 142
Perform pseudo-color processing on the second multiply image to produce a second pseudo-color processed image 145
Perform brightness and/or contrast adjustment on the first pseudo-color processed image 147
Perform brightness and/or contrast adjustment on the second pseudo-color processed image 160
Integrate the second pseudo-color processed image, the first pseudo-color processed image and the first image to produce a second integrated image

FIG. 4

ENDOSCOPIC IMAGE PROCESSING METHOD

CROSS-REFERENCE TO RELATED APPLICATION

This application claims the priority benefit of U.S. provisional application Ser. No. 63/658,451, filed on Jun. 11, 2024, and China application serial no. 202411326627.6, filed on Sep. 23, 2024. The entirety of each of the above-mentioned patent applications is hereby incorporated by reference herein and made a part of this specification.

BACKGROUND

Technical Field

The invention relates to an image processing method, and particularly relates to an endoscopic image processing method.

Description of Related Art

Current clinical endoscope mainly uses visible light images, and endoscopes of different diameters are used for different tissues and expected treatment methods. How to improve the image quality of endoscope in a detected area to meet the needs of medical clinical images is a research direction of this field.

SUMMARY

The invention is directed to an endoscopic image processing method, which acquires images with a plurality of bands or polarized angles of a same area, and improves endoscopic image quality of diseased parts by processing and integrating these images.

An embodiment of the invention provides an endoscopic image processing method suitable for using an endoscope to capture images of diseased parts, which comprises following steps: providing a first image and a second image of the diseased parts, wherein wavelengths or polarized angles of the first image and the second image are different; performing binary image processing on the second image; performing multiply processing on the second image to produce a first multiply image according to a result of the binary image processing; performing pseudo-color processing on the multiply image to produce a first pseudo-color processed image; and integrating the first pseudo-color processed image with the first image to produce a first integrated image.

In an embodiment of the invention, before performing the binary image processing on the second image, the method further comprises performing brightness and/or contrast adjustment on the second image.

In an embodiment of the invention, before performing the pseudo-color processing on the first multiply image, the method further comprises performing contrast adjustment on the first multiply image.

In an embodiment of the invention, before integrating the first pseudo-color processed image with the first image, the method further comprises performing brightness and/or contrast adjustment on the first pseudo-color processed image.

In an embodiment of the invention, the first image is a visible light image, and the second image is a near-infrared light image, a short-wave infrared light image, or a polarized light image.

In an embodiment of the invention, the endoscope image processing method further comprises: providing a third image of the diseased parts, where wavelengths or polarized angles of the first image, the second image and the third image are different; performing binary image processing on the third image; and performing multiply processing on the third image according to a result of the binary image processing of the third image to produce a second multiply image; performing pseudo-color processing on the second multiply image to produce a second pseudo-color processed image; and integrating the second pseudo-color processed image, the first pseudo-color processed image and the first image to produce a second integrated image.

In an embodiment of the invention, before performing binary image processing on the third image, the method further comprises performing brightness and/or contrast adjustment on the third image.

In an embodiment of the invention, before performing the pseudo-color processing on the second multiply image, the method further comprises performing contrast adjustment on the second multiply image.

In an embodiment of the invention, before integrating the second pseudo-color processed image, the first pseudo-color processed image and the first image, the method further comprises performing the brightness and/or contrast adjustment on the second pseudo-color processed image.

In an embodiment of the invention, the first image is a visible light image, and the second image and the third image are two of a near-infrared light image, a short-wave infrared light image, and a polarized light image.

The endoscopic image processing method of the invention provides a first image and a second image of diseased parts with different wavelengths or polarized angles, and performs binary image processing on the second image. According to the result of the binary image processing, multiply processing is performed on the second image to produce a first multiply image. Pseudo-color processing is performed on the first multiply image to produce a first pseudo-color processed image. Finally, the first pseudo-color processed image is integrated with the first image to produce a first integrated image. Since the endoscopic image processing method acquires images with a plurality of bands or polarized angles of a same area, endoscopic image quality of the diseased parts is effectively improved by processing and integrating these images.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is a schematic flowchart of an endoscopic image processing method according to an embodiment of the invention.

FIG. 4 is a schematic flowchart of an endoscopic image processing method according to another embodiment of the invention.

DESCRIPTION OF THE EMBODIMENTS

Figure 2:
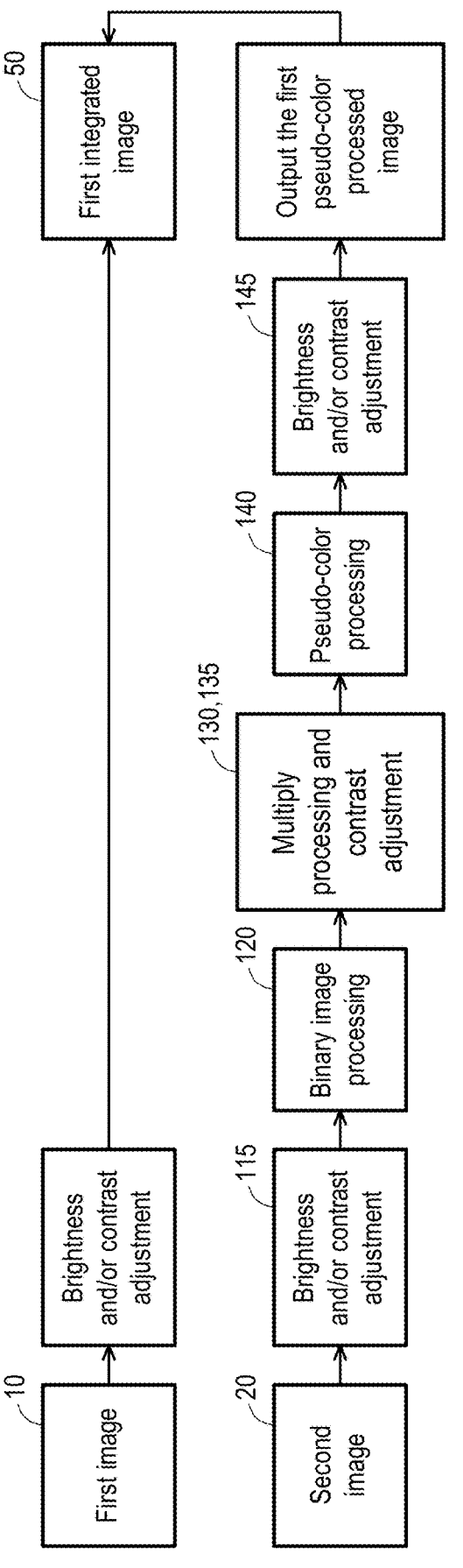
FIG. 2 is a block diagram of FIG. 1.

Reference will now be made in detail to the present preferred embodiments of the invention, examples of which are illustrated in the accompanying drawings. Wherever possible, the same reference numbers are used in the drawings and the description to refer to the same or like parts.

Figure 3:
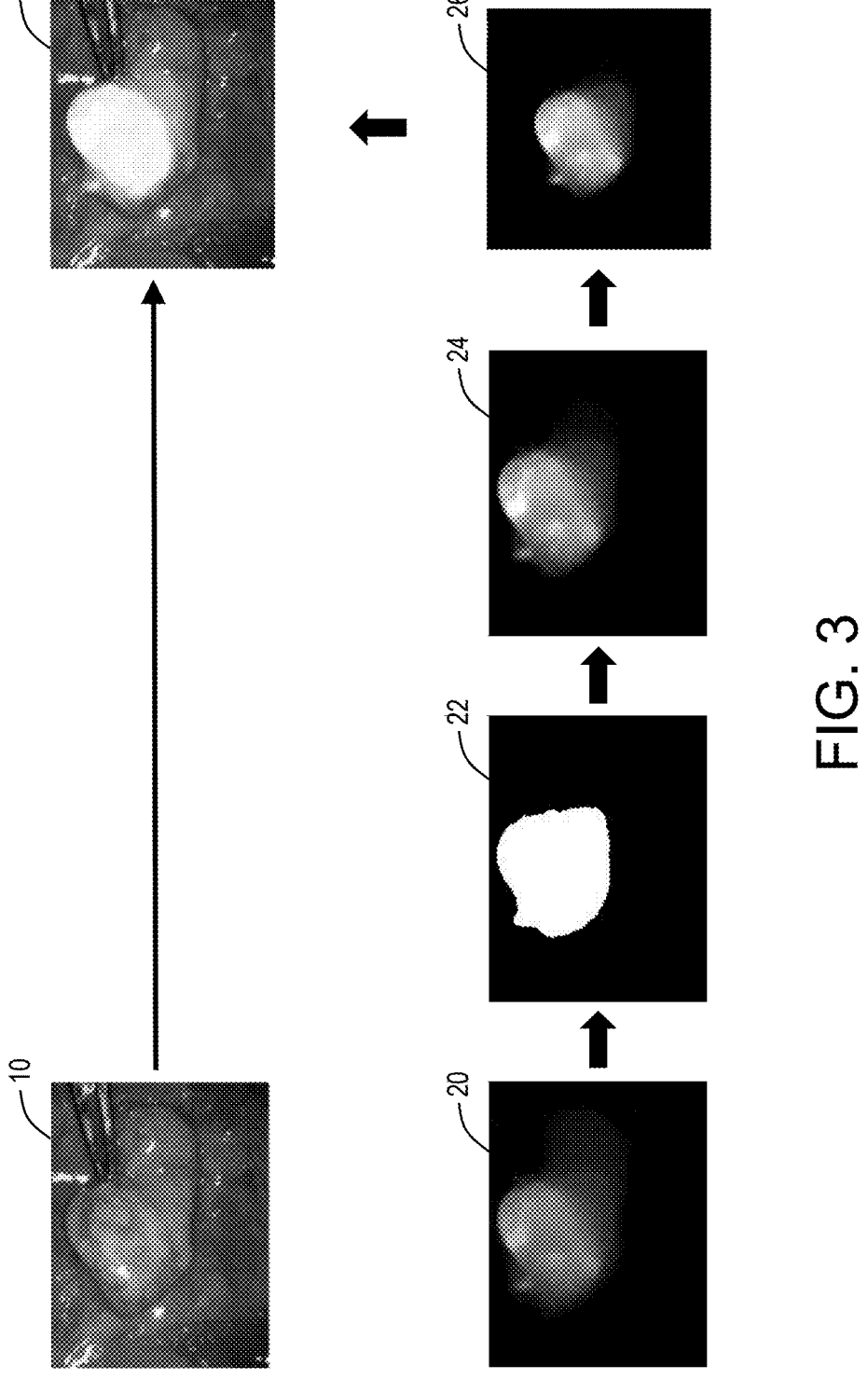
FIG. 3 is an actual image diagram of FIG. 2.

FIG. 1 is a schematic flowchart of an endoscopic image processing method according to an embodiment of the invention. FIG. 2 is a block diagram of FIG. 1. FIG. 3 is an actual image diagram of FIG. 2.

Referring to FIG. 1 to FIG. 3, the endoscopic image processing method 100 of the embodiment is adapted to capture images of diseased parts by using an endoscope, and by integrating images captured by a plurality of light sources, differences between the diseased parts and other tissues may be enhanced to assist doctors in making better judgments.

The endoscopic image processing method 100 of the embodiment comprises following steps. First, in step 110, a first image 10 and a second image 20 of diseased parts are provided, where wavelengths or polarized angles of the first image 10 and the second image 20 are different. For example, the first image 10 is a visible (VIS) light image, and the second image 20 is a near-infrared (NIR) light image, a short-wave infrared (SWIR) light image, or a polarized light image.

In the embodiment, the second image 20 is, for example, a near-infrared light (700-1100 nm) image. As shown in FIG. 3, the second image 20 is a grayscale image, which only presents a signal intensity.

Near-infrared light may be used with fluorescent developers in human body. The fluorescent developers are mainly ICG (Indocyanine green). The near-infrared light excites ICG to produce fluorescence. A wavelength of the near-infrared light is about 780-800 nm, while a wavelength of fluorescence is about 820 nm. Images of the near-infrared light may be captured through most image sensors (silicon-based image sensors), so that images of different bands may be obtained through filters of different bands.

According to characteristics of light, penetration depths of light on different tissues in the human body are different. The penetration depth of photons is affected by composition of each layer of tissues in each organ. For example, a mucosal tissue of the digestive tract is completely different from that of the skin layer. For example, in terms of penetration depths of 400-1800 nm light in the skin and the mucosal tissue, the tissue images may be obtained with the near-infrared light from a deeper layer than visible light and short-wave infrared light.

For example, a wavelength of green light is about 500 nm, and its penetration depth in mucosal tissue is about 1 mm. However, if ICG is excited by the near-infrared light of 800 nm, a fluorescent image thereof may be taken to a depth of about 5 mm. Since a metabolic rate of ICG in tumors and some tissues is smaller than that in normal tissues, a larger amount of ICG will remain in the tumor tissue, which may be used to obtain the image of deeper layer tumors in mucosa, and a concentration difference of ICG in blood vessels and tissues may also be used to label blood vessels.

Therefore, through the characteristics that near-infrared light is used to create ICG fluorescence, it may assist in learning a distribution of tumor in deeper layers. Additionally, polarization images of visible or near-infrared light may also be used to provide more images related to a boundary between mucosa and tumor tissues.

Although short-wave infrared light cannot reach the depth of near-infrared light, and cannot effectively label specific cells or tumors via fluorescent materials like ICG, for the tissue image of short-wave infrared, this technology is dependent on the absorption characteristic of substances for special wavelength without additional developer.

In addition, application of polarized light images has been used in biological tissues, especially cancerous and cardio-vascular tissues. Collagen is the main component of human, and since collagen is a non-centrosymmetric structural material, it reacts with the polarized light and responds onto the polarized image. Therefore, the application of polarized images in endoscopes is also valuable, which may help to provide boundary information between tumors/plaques and tissues, so this will help doctors more effectively understand boundaries when performing endoscopic treatment, and confirm whether blood vessel walls are affected when removing plaque.

Namely, a designer may select an appropriate type of light according to a type of the diseased parts, so as to better detect the diseased parts.

The first image 10 (visible light image) is still used as a main image in the invention, and the second image 20 (near-infrared light, short-wave infrared light or polarized light image) is superimposed on the first image 10 (visible light image) after feature processing to obtain an integrated image for the doctor to more effectively determine the diseased parts.

Certainly, in other embodiments, the number of images is, for example, not two, in terms of arterial embolism, the first image 10 may be a visible light image, the second image 20 may be a short-wave infrared light image, and the third image 30 (FIG. 5) may be a polarized light image. In terms of tumor images, the first image 10 may be a visible light image, the second image 20 may be a near-infrared light image, and the third image 30 may be a polarized light image. In terms of tissue blood leakage, the first image 10 may be a visible light image, and the second image 20 may be a short-wave infrared light image. The above combinations may obtain images of the diseased parts that are more conducive to treatment after image processing and integration.

Following the step 110, the endoscopic image processing method 100 may optionally comprise step 115 of performing brightness and/or contrast adjustment on the second image 20. As shown in FIG. 2, in the embodiment, the brightness and/or contrast adjustment of the first image 10 may also be optionally performed.

Then, in step 120, binary image processing is performed on the second image 20. As shown in FIG. 3, after the binary image processing, a binary image processing image 22 is produced, that is, an image with only black and white but no grayscale image is produced.

Then, in step 130, multiply processing is performed on the second image 20 to produce a first multiply image 24 according to a result of the binary image processing. In step 130, a white portion of the second image 20 corresponding to the binary image processing image is retained, and a black portion of the second image 20 corresponding to the binary image processing image is replaced to black, as the purpose is to produce the first multiply image 24 with clearer edges.

Following the step 130, the endoscopic image processing method 100 may optionally comprise step 135 of performing contrast adjustment on the first multiply image 24.

Then, in step 140, the pseudo-color processing is performed on the first multiply image 24 to produce a first pseudo-color processed image 26. As shown in FIG. 3, the pseudo-color processing may pseudo a new color that is out of all the colors in the first image 10 (for example, blue or yellow-green, etc.) to make the diseased parts more clearly highlighted during subsequent integration.

Following the step 140, the endoscopic image processing method 100 may optionally comprise step 145 of performing brightness and/or contrast adjustment on the first pseudo-color processed image 26.

Finally, in step 150, the first pseudo-color processed image 26 is integrated with the first image 10 to produce a first integrated image 50. As shown in FIG. 3, the tumor in the first integrated image 50 is more clearly indicated by light blue color.

Figure 5:
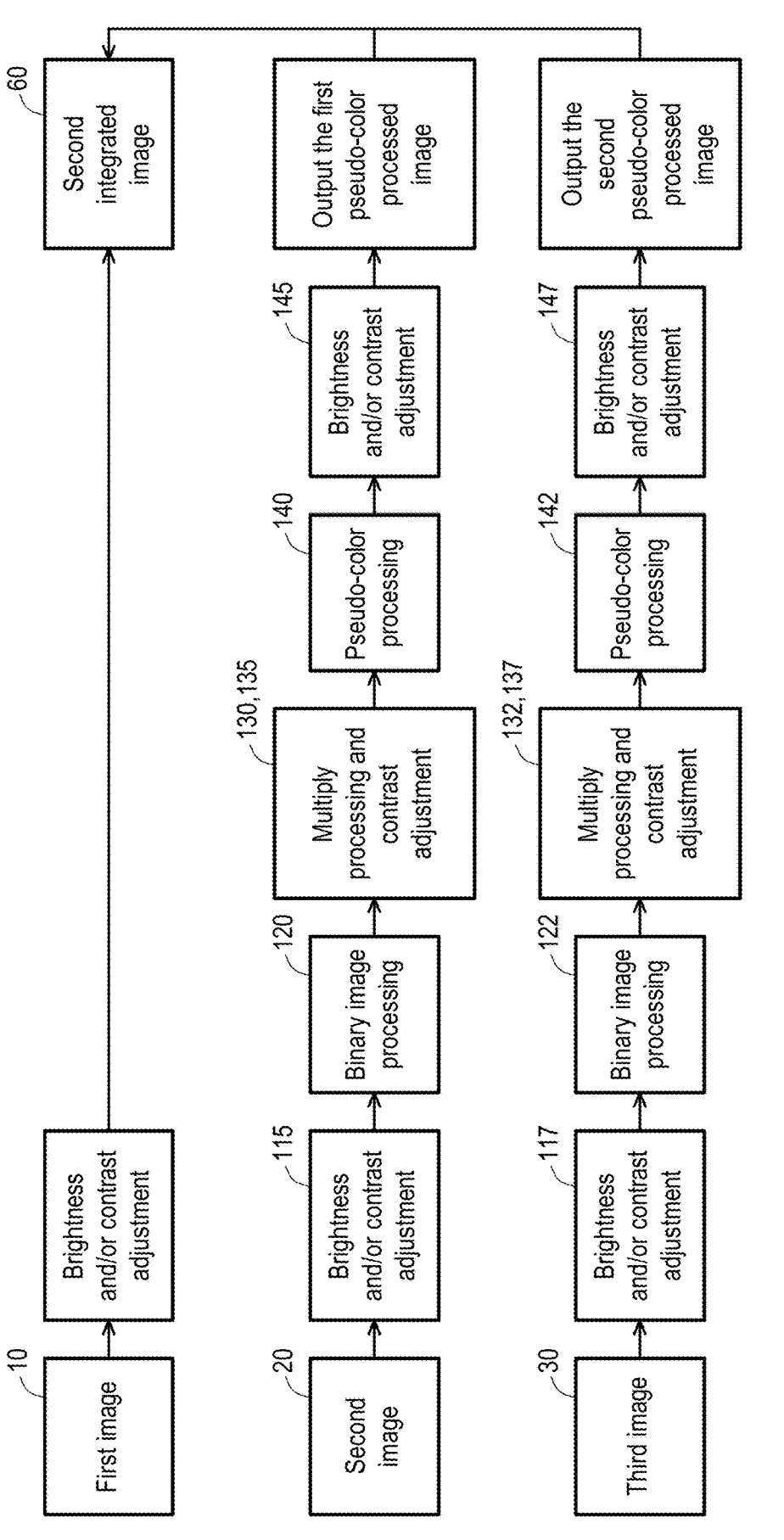
FIG. 5 is a block diagram of FIG. 4.

FIG. 4 is a schematic flowchart of an endoscopic image processing method according to another embodiment of the invention. FIG. 5 is a block diagram of FIG. 4. Referring to FIG. 4 and FIG. 5, a main difference between an endoscopic image processing method 100a of FIG. 4 and the endoscopic image processing method 100 of FIG. 1 is that the endoscopic image processing method 100a of FIG. 4 integrates three images, and the endoscopic image processing method 100a further comprises the following steps.

In step 112, a third image 30 of the diseased parts is provided, where wavelengths or polarized angles of the first image 10, the second image 20 and the third image 30 are different. The first image 10 is a visible light image, and the second image 20 and the third image 30 are two of a near-infrared light image, a short-wave infrared light image and a polarized light image.

In terms of arterial embolism, the first image 10 may be a visible light image, the second image 20 may be a short-wave infrared light image, and the third image 30 may be a polarized light image. In terms of tumor images, the first image 10 may be a visible light image, the second image 20 may be a near-infrared light image, and the third image 30 may be a polarized light image. Certainly, the types of the first image 10, the second image 20, and the third image 30 are not limited thereto.

Following the step 112, the endoscopic image processing method 100a may optionally comprise step 117 of performing brightness and/or contrast adjustment on the third image 30. Then, in step 122, binary image processing is performed on the third image 30. Then, in step 132, multiply processing is performed on the third image 30 according to a result of the binary image processing of the third image 30 to produce a second multiply image.

Following the step 132, the endoscopic image processing method 100a may optionally comprise step 137 of performing contrast adjustment on the second multiply image. Then, in step 142, pseudo-color processing is performed on the second multiply image to produce a second pseudo-color processed image.

Following the step 142, the endoscopic image processing method 100a may optionally comprise step 147 of performing brightness and/or contrast adjustment on the second pseudo-color processed image. Finally, in step 160, the second pseudo-color processed image, the first pseudo-color processed image 26 and the first image 10 are integrated to produce a second integrated image 60.

Similarly, a main image of the embodiment is, for example, the first image 10 (visible light image), and the second image 20 and the third image 30 (two of the near-infrared light, short-wave infrared light and polarized light images) are superimposed on the first image 10 (visible light image) after feature processing to obtain an integrated image for the doctor to more effectively determine the diseased parts.

The endoscopic image processing method of the invention provides a first image and a second image of diseased parts with different wavelengths or polarized angles, and performs binary image processing on the second image. According to the result of the binary image processing, multiply processing is performed on the second image to produce a first multiply image. Pseudo-color processing is performed on the first multiply image to produce a first pseudo-color processed image. Finally, the first pseudo-color processed image is integrated with the first image to produce a first integrated image. Since the endoscopic image processing method acquires images with a plurality of bands or polarized angles of a same area, by processing and integrating these images, endoscopic image quality of the diseased parts is effectively improved.

Finally, it should be noted that the above embodiments are only used to illustrate the technical solution of the disclosure rather than limit it. Although the disclosure has been described in detail with reference to the foregoing embodiments, those of ordinary skill in the art should understand that: the technical solutions described in the foregoing embodiments may still be modified, or some or all of the technical features may be equivalently replaced; and these modifications or substitutions do not cause the essence of the corresponding technical solution to depart from the scope of the technical solution of each embodiment of the disclosure.

What is claimed is:

1. An endoscopic image processing method, suitable for using an endoscope to capture images of diseased parts and performed by a computer processor, and comprising:
   providing a first image and a second image of the diseased parts, wherein wavelengths or polarized angles of the first image and the second image are different;
   performing binary image processing on the second image by the computer processor;
   performing a processing of multiply blend mode on the second image to produce a first multiply image according to a result of the binary image processing by the computer processor, wherein in the processing of multiply blend mode on the second image, a white portion of the second image corresponding to the binary image processing image is retained, and a black portion of the second image corresponding to the binary image processing image is replaced to black;
   performing pseudo-color processing on the first multiply image to produce a first pseudo-color processed image by the computer processor; and
   integrating the first pseudo-color processed image with the first image by the computer processor to produce a first integrated image configured to display for determining a condition of the diseased parts.

2. The endoscopic image processing method as claimed in claim 1, wherein before performing the binary image processing on the second image, the endoscopic image processing method further comprises:
   performing brightness and/or contrast adjustment on the second image by the computer processor.

3. The endoscopic image processing method as claimed in claim 1, wherein before performing the pseudo-color processing on the first multiply image, the endoscopic image processing method further comprises:
   performing contrast adjustment on the first multiply image by the computer processor.

4. The endoscopic image processing method as claimed in claim 1, wherein before integrating the first pseudo-color processed image with the first image, the endoscopic image processing method further comprises:
   performing brightness and/or contrast adjustment on the first pseudo-color processed image by the computer processor.

5. The endoscopic image processing method as claimed in claim 1, wherein the first image is a visible light image, and the second image is a near-infrared light image, a short-wave infrared light image, or a polarized light image.

6. The endoscopic image processing method as claimed in claim 1, further comprising:

providing a third image of the diseased parts, wherein wavelengths or polarized angles of the first image, the second image and the third image are different;

performing binary image processing on the third image by the computer processor;

performing the processing of multiply blend mode on the third image according to a result of the binary image processing of the third image to produce a second multiply image by the computer processor, wherein in the processing of multiply blend mode on the third image, a white portion of the third image corresponding to the binary image processing image is retained, and a black portion of the third image corresponding to the binary image processing image is replaced to black;

performing pseudo-color processing on the second multiply image to produce a second pseudo-color processed image by the computer processor; and integrating the second pseudo-color processed image, the first pseudo-color processed image and the first image by the computer processor to produce a second integrated image for display.

7. The endoscopic image processing method as claimed in claim 6, wherein before performing the binary image processing on the third image, the endoscopic image processing method further comprises:

performing brightness and/or contrast adjustment on the third image by the computer processor.

8. The endoscopic image processing method as claimed in claim 6, wherein before performing the pseudo-color processing on the second multiply image, the endoscopic image processing method further comprises:

performing contrast adjustment on the second multiply image by the computer processor.

9. The endoscopic image processing method as claimed in claim 6, wherein before integrating the second pseudo-color processed image, the first pseudo-color processed image and the first image, the endoscopic image processing method further comprises:

performing brightness and/or contrast adjustment on the second pseudo-color processed image by the computer processor.

10. The endoscopic image processing method as claimed in claim 6, wherein the first image is a visible light image, and the second image and the third image are two of a near-infrared light image, a short-wave infrared light image, and a polarized light image.

\* \* \* \* \*